United States Patent
Bhaskaran et al.

(10) Patent No.: US 7,179,930 B2
(45) Date of Patent: Feb. 20, 2007

(54) PROCESS FOR ISOLATING, PURIFYING AND FORMULATING A STABLE, COMMERCIAL GRADE LUTEIN PASTE FROM OLEORESIN

(75) Inventors: Sunil Bhaskaran, Pune (IN); Vishwaraman Mohan, Pune (IN)

(73) Assignee: Indus Biotech Private Limited, Pune (IN)

( * ) Notice: Subject to any disclaimer, the term of this patent is extended or adjusted under 35 U.S.C. 154(b) by 171 days.

(21) Appl. No.: 11/038,564

(22) Filed: Jan. 18, 2005

(65) Prior Publication Data

US 2005/0182280 A1 Aug. 18, 2005

Related U.S. Application Data

(60) Provisional application No. 60/537,042, filed on Jan. 16, 2004.

(51) Int. Cl.
*C11B 7/00* (2006.01)
(52) U.S. Cl. ............... 554/198; 554/206; 554/224
(58) Field of Classification Search ........... 554/224, 554/198, 206
See application file for complete search history.

(56) References Cited

U.S. PATENT DOCUMENTS

| 5,382,714 A | 1/1995 | Khachik |
| 5,648,564 A | 7/1997 | Ausich et al. |
| 5,876,782 A | 3/1999 | Sas et al. |
| 6,262,284 B1 | 7/2001 | Khachik |
| 6,380,442 B1 | 4/2002 | Madhavi et al. |
| 6,504,067 B1 | 1/2003 | Montoya-Olvera et al. |

FOREIGN PATENT DOCUMENTS

GB 555636 9/1943

*Primary Examiner*—Deborah D. Carr
(74) *Attorney, Agent, or Firm*—Merchant & Gould P.C.

(57) ABSTRACT

The present invention relates to a process for obtaining stabilized Lutein with about 95% yield from oleoresin at ambient temperature, said process comprising steps of dissolving cleaned oleoresin in alcohol to obtain dissolved Xanthophylls esters as clear solution on filtration, cleaning dissolved oleoresin comprising xanthophylls esters in ion-exchange resin, hydrolyzing the clear solution with base in presence of phase-transfer catalyst in alcohol medium, quenching the hydrolyzed solution in water maintaining acidic pH to obtain undissolved solids on filtration, dissolving the solids in ester to obtain ester layer on filtration, drying ester layer to obtain semi-solid residue, triturating the semi-solid residue in alcohol whereby obtaining lutein crystals of about 65% assay and an alcoholic fraction, distilling the alcoholic fraction to obtain non water-soluble fractions, and mixing the Lutein crystals with non water-soluble fractions to obtain a stable Lutein paste.

21 Claims, No Drawings

PROCESS FOR ISOLATING, PURIFYING AND FORMULATING A STABLE, COMMERCIAL GRADE LUTEIN PASTE FROM OLEORESIN

FIELD OF THE PRESENT INVENTION

The present invention relates to a process for obtaining stabilized Lutein with about 95% yield from oleoresin at ambient temperature. The lutein crystals are mixed with non water-soluble fractions to obtain a stable Lutein paste. Its is a method of separation, method of purification, and method of stabilization without use of any additives

BACKGROUND OF THE PRESENT INVENTION

Carotenoids are fat-soluble group of naturally occurring plant pigments. Carotenoids can be divided in to two main categories: Carotenes and Xanthophylls. Carotenes refer to Carotenoids, which contain only carbon and hydrogen atom, e.g. Beta Carotene, Alpha Carotene and Lycopene. Xanthophylls refer to compounds that contain an additional hydroxyl group or Keto group or both. E.g. Lutein, Zeaxanthin.

Several studies have shown that consumption of fruit and vegetable rich in Carotenoids can offer protection against Cancer, Cardiovascular and eye diseases. Since humans cannot make Carotenes, they depend upon the diet or supplementation as the source of these important nutrients. Carotenoids have been found to possess potential membrane antioxidants activity due to their reactivity with singlet oxygen and oxygen free radicals. Singlet oxygen has been implicated in biological systems and is capable of damaging proteins, lipids and DNA. The anti-cancer activity of carotenoids is attributable to the anti-oxygen activity of carotenoids. Lutein is an important compound belonging to the group of Carotenoids. Scientific studies show that Lutein plays a significant role in:

1. Prevention of Age related Macular degeneration of the eye.
2. Prevention of Colon Cancer.

Free radicals generated in the body during metabolism damage eye (more in the case of diabetes). Delicate tissues of the eye contain mainly polyunsaturated fatty acids. They are very vulnerable to damage by free radicals and oxidative stress. In healthy eye tissues large nutrients of antioxidants including Lutein exist to counter this damage. Various published studies suggest that intake of Lutein or caroteniods can lower eye diseases.

Lutein and Zeaxanthin are highly concentrated in the Macula of eye. Macula is a small area of retina responsible for central vision and high visual acuity. The Yellow pigment of Macula consisting of Lutein and Zeaxanthin protect the macula form the damages of photoxidative effect of UV blue light. The human body metabolise Lutein to Zeaxanthine. Lutein Intake increases the serum level of Lutein and Zeaxanthin and improves the function of UV blue blocking and protection. Therefore Lutein is emerging as an important nutrient for better health and prevention of Disease. There is increasing demand for Lutein supplements from the aging population of the World.

Carotenoids are present as plant pigments. They are very readily obtained from flowers (Marigold—*Tagatea erecta*), fruits (berries, tomatoes), and roots (Carrots, Yellow Potatoes). The hydroxyl caroteniods are found as esters in the combined form. They usually appear as diesters of lauric, myristic and Palmitic Acid. In this form, they are very stable. However, the Lutein esters (such as dipalmitate of Lutein from Marigold) is not found in human serum.

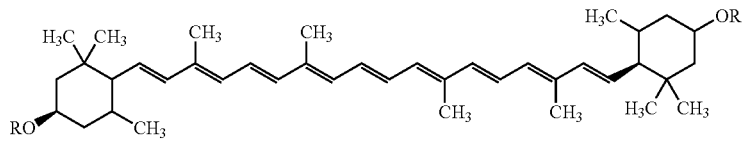

R=Palmitic, Myristic or Lauric Acid

STRUCTURE OF XANTHOPHYLL

Therefore, Xanthophyll is an ester of Lutein with chemical combination with Palmitic acid as indicated by "R". With alkali hydrolysis the R (Palmitic acid) gets removed with the formation of free Lutein (which is an alcohol) as below.

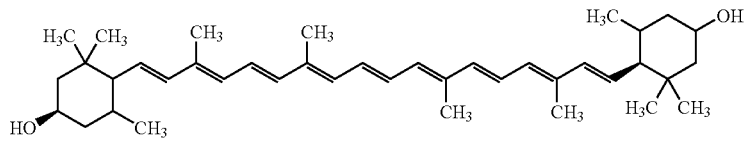

LUTEIN

They partially undergo hydrolysis and only Lutein is absorbed into the serum. Therefore it is important to provide free Lutein as supplement for bioavailability. However, Lutein in its free form is highly vulnerable to degradation due to exposure to heat and oxidation. Lutein does not remain stable during storage. Lutein gets converted into epoxide of Lutein due to air oxidation. Therefore, the real challenge here is how to stabilise Lutein to improve shelf life and how to minimize loss of Lutein during the Hydrolysis reaction. Stabilization without the use of chemicals will be very important. There is an important need to create a process for formation of free Lutein, which is not exposed to temperature and long processes and that can be made stable with natural stabilizing material without using any chemical additives.

Lutein is currently available in the form of granules of 5%, 10% and in the form of stable pastes at 10%, 20% and 30% assay level Free pure. Lutein at assay of 90% is not stable. It gets instantly oxidized to its epoxide. This epoxide is not having any useful biological property. Lutein is normally stabilised by adding chemical additives and is made available in assays ranging from 5% to 30% This is stabilized with the addition of external stabilizing compounds such as Sorbic acid, Sodium Benzoate, Polysorbate, Polyethylen glycol, HPMC (hydroxypropyl Methyl cellulose), tocopherols, Rosemarie extracts, vegetable oils. Even if pure Lutein is prepared, it gets diluted by the addition or preservatives and stabilizing agents .to levels as mentioned above during stabilization. Many of these stabilizing chemicals are very expensive too. Commercially available Lutein is at very prohibitively high prices due to its problems of stabilization, cumbersome process for preparation and poor yields in manufacture due to its inherent instability.

In U.S. Pat. No. 5,382,714 (Frederick Khaschik), a method has been disclosed for isolation, purification and recrystallisation of Lutein from a Saponified Marigold oleoresin obtained under the Trademark KEMIN YELLOW oil form KEMIN INDUSRIES, Inc, Des Moines Iowa. This patent has a major disadvantage in that it does not specify an efficient method for release of Lutein from the esters as appearing in the plant. It provides a method of isolation of existing free Lutein in the input material. It perpetuates the inefficiency of transesterification as done in the input raw material. This patent does not say anything about ester breaking process. Besides, the process of purification suggested involves multiple solvents and temperature of −20° C. This does not lend itself as a commercially viable process.

U.S. Pat. No. 5,648,564 (Ausich et al) discloses a process for saponification of Lutein ester and purification of free Lutein. This process has 3 major disadvantages:
1. Saponification is carried out at high temperature of 65° C. to 80° C. This is high enough to cause degradation of Lutein.
2. Saponification process time is typically at least 3 hours. Therefore the reaction time is long. This combined with temperature leads to further degradation of Lutein.
3. The reaction is carried out in Propylene glycol and Ethanol and aqueous alkali. The reaction mixture produced is a very viscous soapy material due to the presence of water in the reaction mixture. It is very well known that Lutein occurs as minute crystals during the aqueous phase saponification reaction of marigold oleoresin. This minute crystals get dispersed in the viscous mixture. The separation process suggested in the patent does not efficiently recover all free Lutein.

Therefore, this process is not a very efficient cost effective commercial process.

U.S. Pat. No. 5,876,782 (Sas et al) describes a process for converting non-free form of Xanthophyl to free xanthophylls in the biomass. This process is suitable for low percentage of Lutein generation in biomass Here again the process suffers from the disadvantage of high temperature (69 degrees C.) and long process time of 10 hours. Both these conditions are harsh and cause degradation of Lutein. This material is only suitable for animal or poultry feed. As such is not suitable for human consumption.

U.S. Pat. No 6,262,784 B 1 (Khachik) describes a process for simultananly extracting, saponifying and isolating Lutein and Zeaxanthin in high purity from plant without the use of harmful organic solvents. This process has very large volumes of solvent for extraction and saponification. The solvent tetrahydrofuran is observed to degrades and produce Peroxides. This Peroxide can degrade the carotenoid. The carotenoid in plant material is usually low at 1% to 2%. This low concentration of Xanthophylls and the need to use high volume of solvent make the process not very cost effective. The meal to solvent ratio is 1:20 and total extractable to solvent ratio is 1:1000. This makes the commercial viability of the process doubtful.

U.S. Pat. No. 6,380,442 B 1 (Madhavi et al) describes a process for isolating and purifying mixed carotenoids containing high concentration of specific compounds. The process employs the hydrolysis of marigold oleoresin using isopropanol, water and alkali at 60 to 65° C. for a period of 90 minutes. While this process is certainly better than the previous process in temperature and duration, it still suffers from the following disadvantages:
1. The hydrolysis temperature of 65° C. is high and causes Lutein degradation.
2. The reaction time of 90 minutes is still long and leads to oxidation at this temperature.
3. The free Lutein released during the aqueous phase hydrolysis is always very minute crystals and they disperse in the slimy soapy solution. Presence of aqueous alkali makes the reaction mixture very viscous. The process doe not offer a commercially viable separation method for efficient recovery of free Lutein. It is very difficult to remove all precipitated crystals of Lutein from the thick slimy soapy mixture as per the suggested method.

U.S. Pat. No. 6,504,067 B 1 (Montoya et al) describes a patent for cleaning of oleoresin with alkali and acid. This cleaned oleoresin is subjected to Aqueous alkali hydrolysis at a temperature of 90° C. for a period of 8 hours in presence of certain emulsifiers for effective contact. This process also suffers form disadvantage of high temperature and long cycle time leading to degradation of free Lutein along with separation issues as described above.

In view of the increasing demand for Commercial Lutein as 10%, 20% or 30% product, there exists a need for no water, a room temperature, low exposure time hydrolysis method for release of free Lutein and its separation from its esters that can be made stable during storage without the use of any chemical additives. These minute crystals of Lutein need to be separated effectively from the fatty acid soap matrix to increase the overall yield. If the above-mentioned features are addressed, one can develop a cost effective commercially viable process, which will minimize Lutein degradation due to temperature and oxidation and improve yield by releasing free Lutein from minimum soapy mass. This Lutein can be stabilized by a novel method without adding any additives. This Lutein can be made available as Commercial Lutein at 10%, 20% and 30% assay levels at viable prices.

OBJECTS OF THE PRESENT INVENTION

The present invention relates to a process for obtaining stabilized Lutein.

Another object of the present invention is to develop a process for obtaining high yield of pure lutein.

Yet another object of the present invention relates to develop a process for obtaining lutein at ambient temperature, without spending on heat energy.

Still another object of the present invention relates to develop a process for obtaining lutein wherein the lutein obtained is a stable lutein of about 35% assay.

Still another object of the present invention relates to develop a process for obtaining lutein, which is stabile at ambient conditions for at least few months 6 without any degradation.

Still another object of the present invention relates to develop a process for obtaining lutein, wherein the lutein stays at normal storage conditions and is amenable for commercial applications.

SUMMARY OF THE PRESENT INVENTION

The present invention provides a novel method for hydrolysis of xanthophyll into Lutein without the use of water, at low temperature and with minimum reaction time using phase transfer Catalysts. The declared invention provides a very efficient method for separation of fine crystalline Lutein that get scattered in the matrix of the soap that is produced during the hydrolysis. The proposed method minimizes the formation of soap.

In accordance with certain embodiments of the present Invention, a very compact and cost effective method for the production of free and stable Lutein is provided, preferably in commercial products purity of 10%, 20% and 30% assay level. This invention offers a process which minimize the degradation of temperature labile Lutein by accomplishing these processes in low temperature and in shorter time cycles and also a method for stabilizing this Lutein without any additives and helps to make commercial grades of Lutein.

DETAILED DESCRIPTION OF THE PRESENT INVENTION

Accordingly, the present invention relates to a process for obtaining stabilized Lutein with about 95% yield from oleoresin at ambient temperature, said process comprising steps of dissolving cleaned oleoresin in alcohol to obtain dissolved Xanthophylls esters as clear solution on filtration, cleaning dissolved oleoresin comprising xanthophylls esters in ion-exchange resin, hydrolyzing the clear solution with base in presence of phase-transfer catalyst in alcohol medium, quenching the hydrolyzed solution in water maintaining acidic pH to obtain undissolved solids on filtration, dissolving the solids in ester to obtain ester layer on filtration, drying ester layer to obtain semi-solid residue, triturating the semi-solid residue in alcohol whereby obtaining lutein crystals of about 65% assay and an alcoholic fraction, distilling the alcoholic fraction to obtain non water-soluble fractions, and mixing the Lutein crystals with non water-soluble fractions to obtain a stable Lutein paste.

In an embodiment of the present invention, wherein the invention relates to process for obtaining stabilized Lutein with about 95% yield from oleoresin at ambient temperature, said process comprising steps of:
  a. dissolving cleaned oleoresin in alcohol to obtain dissolved Xanthophylls esters as clear solution on filtration,
  b. cleaning dissolved oleoresin comprising xanthophylls esters in ion-exchange resin,
  c. hydrolyzing the clear solution with base in presence of phase-transfer catalyst in alcohol medium,
  d. quenching the hydrolyzed solution in water maintaining acidic pH to obtain undissolved solids on filtration,
  e. dissolving the solids in ester to obtain ester layer on filtration,
  f. drying ester layer to obtain semi-solid residue,
  g. triturating the semi-solid residue in alcohol whereby obtaining lutein crystals of about 65% assay and an alcoholic fraction,
  h. distilling the alcoholic fraction to obtain non water-soluble fractions,
  i. mixing the Lutein crystals of step (g) with non water-soluble fractions of step (h) to obtain a stable Lutein paste.

In another embodiment of the present invention, wherein the alcohol is selected from a group comprising methanol, ethanol, propanol, butanol and pentanol.

In yet another embodiment of the present invention, wherein alcohol used in the process is butanol.

In still another embodiment of the present invention, wherein the ion exchange resin used in the process is a strong base anion resin.

In still another embodiment of the present invention, wherein the base is in powder form selected from a group comprising sodium hydroxide and potassium hydroxide.

In still another embodiment of the present invention, wherein the phase-transfer catalyst as used in the process is a quaternary salt.

In still another embodiment of the present invention, wherein the quaternary salt of the process is selected from a group comprising quarternery phosphonium salt and quarterneryammonium salt.

In still another embodiment of the present invention, wherein the quaternary salts are tetra butyl ammonium bromide and tetra butyl ammonium hydrogen sulphate.

In still another embodiment of the present invention, wherein the ester is selected from a group comprising ethyl acetate, butyl acetate, amyl acetate, and 2-ethyl hexyl acetate.

In still another embodiment of the present invention, wherein the ester used in the process is ethyl acetate.

In still another embodiment of the present invention, wherein quenching the reaction mass with urea.

In still another embodiment of the present invention, wherein the pH is ranging between 3.2 to 4.3

In still another embodiment of the present invention, wherein the maintaining the pH with acetic acid.

In still another embodiment of the present invention, wherein the filtering the solutions with filter paper.

In still another embodiment of the present invention, wherein the oleoresin used in the process is marigold oleoresin.

In still another embodiment of the present invention, wherein the triturating alcohol used in the process is ethyl alcohol.

In still another embodiment of the present invention, wherein the stable lutein used in the process is of about 35% assay.

In still another embodiment of the present invention, wherein the stabilizing material is non-water-soluble fractions of reaction mixture of hydrolysis obtained after distillation of the alcohol.

In still another embodiment of the present invention, wherein the Lutein fraction is blended with non-water-soluble fractions of reaction mixture of hydrolysis to obtain a stable Lutein paste.

In still another embodiment of the present invention, wherein the stabilized Lutein stays at ambient conditions for a period of at least 6 months without any degradation. In still another embodiment of the present invention, wherein the lutein stays at normal storage conditions, amenable for commercial applications.

In the present invention, we have utilized n-butanol as the solvent, as it dissolves the Xanthophyll ester fully and fulfills the above criteria. The Base selected are sodium hydroxide and potassium hydroxide solid powders of 98% and 85% strength respectively.

The phase transfer Catalyst has been chosen from host of compounds comprising of quarterneryphosphonium salts, quarterneryammonium salts, preferably ammonium salts for their ability of ion pair Capabilities. The reaction conditions are developed to suit the hydrolysis mechanism of fatty esters. In the present case care has been taken not to damage the formed Lutein due to excess heat, since the said compounds are thermolabile. The reaction temperature was between 40° C. to 50° C. preferably at 45° C. By maintaining the said condition the reaction period was reduced to 30 mins. At 48° C. the reaction needs only ½ hrs for completion. At 40° C. the period needed was 1 hrs atypical phase transfer condition.

As a pretreatment to remove all free fatty acids of the oleoresin to take care of the free acidity and subsequent viscous soap formation during hydrolysis a treatment with ion exchange resin was introduced at temperatures ranging between 40° C. to 50° C. The resin utilized was a strong base anion exchanger in the form of either gel or macro porous resin. This process helps in minimal creation of soapy matter and in better separation of Lutein.

This process improves Lutein yield.

The isolation was carried out by quenching the reaction mass in DM water containing urea as a complexing agent. This is followed by PH adjustment, filtration, extraction with an ester solvent in which Lutein is soluble. All the water-soluble reaction products such as soapy matter produced, phase transfer catalyst etc., remain in as dissolved in the water phase. The ester removes non-water-soluble products of reaction such as Lutein, free fatty acid, and wax from the original reaction mixture. The said solvents are ethyl acetate, butyl acetate, amyl acetate, 2-ethyl hexyls acetate, preferably ethyl acetate, at temperatures ranging from 15° C. to 50° C. preferably at 40° C. The solvent is evaporated at 45° C. under vacuum.

The resulting paste from the previous process is mixed with 4 to 5 volume of Alcoholic Solvent comprising of single carbon aliphatic to penta carbon straight chain aliphatic alcohols. This is stirred well. Preferably the alcohol used is ethanol, which is amicable for human consumption. The Lutein falls out as a solid. This is filtered and dried in vacuum oven to get Lutein of purity 55% to 60%. The alcoholic fraction is distilled under vacuum fully so as to get a red pasty material. This material consists of the non-water-soluble fraction of the hydrolysis reaction and consist of free fatty acids and wax. This is the residual material from the reaction mass after the release of Lutein as crystals. This is reddish orange in color as it still contains little unseparated Lutein. A surprising discovery has been made that if the purified Lutein is mixed with this fatty acid and wax combination, the Lutein gets stabilized and remains in a stable form without getting oxidized. The Lutein, thus, obtained is blended in to this pasty material by physical mixing in a laboratory ribbon blender. This resultant paste has about 30% Lutein and stays stable beyond 6 months at normal ambient conditions of storage. The free Lutein remains free. It does not chemically combine with fatty acid or wax.

The invention is further elaborated with the help us following examples and should not be construed to limit the scope of the invention.

Experiment 1

50 grams of marigold oleoresin containing 13.8% by weight Lutein ester (Xanthophylls-Marigold Oleoresin) is dissolved in 500 ml of n-butyl alcohol at 40° C. and filtered through filter paper to get a clear solution. This solution is taken in a round bottom 3neck flask attached with thermometer, nitrogen sparge line and the inner temperature adjusted to 45° C. To the above solution. 3.0 Gms of tetra butyl ammonium bromide is added and stirred for 5 minutes. To the above solution 5 grams of sodium hydroxide powder was added and stirred. The inner temperature raises 50° C. due to reaction being exothermic. This is cooled to 45° C. The reaction mass checked for the absence of starting material after ½ hr. The reaction mass was quenched in 5 ltrs of water containing 250 gms of urea. The PH of this solution was adjusted to 3.5 to 4.0 using 80 grams of acetic acid. The reaction mass was filtered through filter paper. The retained solids were dissolved in 250 ml of ethyl acetate at 35° C. and filtered again to remove insolubles. The ethyl acetate layer was dried with anhydrous sodium Sulphate & distilled out below 50° C. to get a semisolid residue .The residue is triturated with 4 to 5 volumes of ethyl alcohol for 4hrs and filtered under nitrogen blanket. The dry Lutein crystals are collected and dried in a vacuum oven at 50° C. After drying the vacuum is released using nitrogen and material is packed in black coloured two layered food grade container. Final weight 6 grams and the assay of the Lutein is 52% by UV Method with an overall yield of 90% Lutein.

Experiment 2

50 grams of marigold oleoresin containing 14.9% by weight Lutein ester(Oleoresin) is dissolved in 500 ml of n-butyl alcohol at 40° C. and filtered through filter paper to get a clear solution. This solution is taken in a round bottom 3neck flask attached with thermometer, nitrogen sparge line and the inner temperature adjusted to 45° C. To the above solution. 3.0 Gms of tetra butyl ammonium hydrogen Sulphate is added and stirred for 5 minutes. To the above solution 5 grams of sodium hydroxide powder was added and stirred. The inner temperature raises 50° C. due to reaction being exothermic. This is cooled to 45° C. The reaction mass checked for the absence of starting material after ½ hr. The reaction mass was quenched in 5 ltrs of water containing 250 gms of urea. The PH of this solution was adjusted to 3.5 to 4.0 using 80 grams of acetic acid. The reaction mass was filtered through filter paper. The retained solids were dissolved in 250 ml of ethyl acetate at 35° C. and filtered again to remove insolubles. The ethyl acetate layer was dried with anhydrous sodium Sulphate & distilled out below 60° C. to get a semisolid residue. The residue is triturated with 4 to 5 volumes of ethyl alcohol for 4 hrs and filtered under nitrogen blanket. The dry Lutein crystals are collected and dried in a vacuum oven at 50° C. After drying the vacuum is released using nitrogen and material is packed in black coloured two layered food grade container. Final weight 5.8 grams of assay of 58% by UV method at a yield of 91%.

Experiment 3

50 grams of marigold oleoresin containing 13.3% by weight Lutein ester(oleoresin) is dissolved in 200 ml of n-butyl alcohol and filtered to get a clear solution. To the above solution50ml of freshly regenerated strong base anion exchange resin is added (e.g. Resin INDION 860). This solution is stirred at 50 ° C. for 2 hrs & cooled, resin filtered off. The resin was washed with 200 ml of butyl alcohol and washings combined with the filtrate. The total filtrate 3 gms of tetra butyl ammonium bromide and 5 gms of powdered sodium hydroxide was added and stirred for 1 hrs at less than 50° C. The reaction is monitored using T.L.C and the work up was carried out as mentioned in the first experiment and final weight is 6 grams having an assay of 52% Lutein with a yield of 94%.

Experiment 4

The above experiments were repeated using 5.3 grams of potassium hydroxide powder in place of Sodium Hydroxide Powder. The final work up was as per the above two experiments. To get 5 grams and 5.5 grams of Lutein respectively of 60% and 58% assay by UV method.

Experiment 5

50 grams of marigold oleoresin containing 14.8% by weight Lutein ester(Oleoresin) is dissolved in 200 ml of n-butyl alcohol and filtered to get a clear solution. To the above solution 50 ml of freshly regenerated strong base an ion exchange resin is added. This solution is stirred at 50 ° C. for 2 hrs & cooled, resin filtered off. The resin was washed with 200 ml of butyl alcohol and washings combined with the filtrate. The total filtrate 3 gms of tetra butyl ammonium hydrogen Sulphate and 5 grams of powdered sodium hydroxide was added and stirred for 1 hrs at less than 50° C. The reaction is monitored using T.L.C and the work up was carried out as mentioned in the first experiment and final weight is 6.1 grams of 54% assay Lutein.

Experiment 6

The above two experiments were repeated using 5.3 gms potassium hydroxide solid in place of sodium hydroxide solid. And the reaction conditions and work up were identical as mentioned in the earlier experiments. The weight of Lutein is 5.9 grams and 5.8 grams respectively of 58.3% and 58% assay.

Experiment 7

50 grams of marigold oleoresin containing 13.4% by weight Lutein ester is dissolved in 200 ml of n-butyl alcohol and filtered to get clear solution at 40° C. To the above Solution under nitrogen atmosphere at 40 to 45° C. added 3.0 grams of tetra butyl Ammonium bromide and stirred for 5 minutes. To the above solution 5 grams of powdered Sodium hydroxide is added under stirring. The inner temperature reached 45° C. in 10 minutes due to exotherm, maintained for ½ hr. After TLC checking and work up in urea & Acetic acid as given in experiment no. 1 to give a paste. This paste was dissolved in 250 ml Ethyl acetate and the water removed by drying the solvent layer using anhydrous sodium Sulphate. The solvent layer is distilled under vacuum at 40° C. to yield 19 grams of pasty material. This paste was mixed with 100 ml of pure Ethyl Alcohol and stored at room temperature till the paste dissolves in to Ethyl Alcohol. Afterwards, the stirring was stopped and it was left to settle. This was filtered to get a Lutein residue after drying of 5.8 grams of 52%. The alcoholic fraction was distilled fully to get a paste of 4.3 grams. This fraction is the non-water-soluble fraction of the reaction products. This essentially consists of fatty acids and wax from the reaction mixture. This material is used as a stabilising agent to stabilize free Lutein by mixing free Lutein with this material. The Lutein was mixed with this paste in a laboratory blender to get a paste of 10.1 grams of Lutein paste. This is free mixture of Lutein with the paste. There is no chemical reaction here. This material was analysed for Free Lutein content by spectrometer and found to be 30.2% Free Lutein. This material was kept for storage stability at 35 to 40° C. in a double-layered Black colored food grade container. In ambient conditions of temperature and humidity (temp from 35 to 40 degrees C. and relative humidity of 49 to 76%) Following are the results:

| | | Duration | | | | | |
|---|---|---|---|---|---|---|---|
| | Initial | 1st Month | 2nd Month | 3rd Month | 4th Month | 5th Month | 6th Month |
| % Lutein | 30.2 | 30.1 | 30.1 | 30.2 | 30.1 | 30.1 | 30.1 |

The above table shows no degradation of Lutein under normal ambient (35 to 40° C.) storage conditions. Free Lutein content is maintained at 30.1% at the end of 6 months. This stable Lutein paste compares with the maximum assay available in commercial grade Lutein. This can be used for the purposes of usage in food and supplements. This also lends itself for conversion to 5% and 10% billets and can be done by anybody skilful in the art.

The lutein is present originally in oleoresin as chemically linked to neighbouring molecules. The hydrolysis of the present invention facilitates isolation of the pure lutein. However, to stabilize the isolated, pure lutein, it is mixed with non-water soluble fraction from the same source of lutein. The interaction is a physical interaction and does not involve any chemical bondage. The lutein is safely present in the matrix and can be used for various desired purposes.

Mixing of lutein with aforementioned fraction does stabilization. There is no chemical reaction. Instead of the usual dangerous chemicals, we have discovered that the part of this natural product can be used as a stabilizing agent. In fact, the inventors themselves were surprised to notice such high stability of lutein, without any significant loss in activity.

The instant invention provides for conditions of Low temperature, and short reaction time. This leads to lessened Lutein damage during reaction. It further enhances the yield.

Further, due to non-usage of water during the isolation process, soap formation is reduced. This also minimizes loss of Lutein.

The stabilized lutein can be safely used in foods and food-supplements.

The instant process obviates the need to stabilize lutein with chemicals, which are expensive. Further, it helps distinguish our process from conventional processes. Thus, the instant process is a much economical process.

The invention claimed is:

1. A process for obtaining stabilized Lutein with about 95% yield from oleoresin at ambient temperature, said process comprising steps of:
   a. dissolving cleaned oleoresin in alcohol to obtain dissolved Xanthophylls esters as clear solution on filtration,
   b. cleaning dissolved oleoresin comprising xanthophylls esters in ion-exchange resin,
   c. hydrolyzing the clear solution with base in presence of phase-transfer catalyst in alcohol medium,
   d. quenching the hydrolyzed solution in water maintaining acidic pH to obtain undissolved solids on filtration,
   e. dissolving the solids in ester to obtain ester layer on filtration,
   f. drying ester layer to obtain semi-solid residue,
   g. triturating the semi-solid residue in alcohol whereby obtaining lutein crystals of about 65% assay and an alcoholic fraction, h. distilling the alcoholic fraction to obtain non water-soluble fractions, and i. mixing the Lutein crystals of step (g) with non water-soluble fractions of step (h) to obtain a stable Lutein paste.

2. A process as claimed in claim 1, wherein the alcohol is selected from a group consisting of methanol, ethanol, propanol, butanol and pentanol.

3. A process as claimed in claim 1, wherein the alcohol is butanol.

4. A process as claimed in claim 1, wherein the ion exchange resin used is strong base anion resin.

5. A process as claimed in claim 1, wherein base is in powder form selected from a group consisting of sodium hydroxide and potassium hydroxide.

6. A process as claimed in claim 1, wherein the phase-transfer catalyst is a quaternary salt.

7. A process as claimed in claim 6, wherein quaternary salt is selected from a group consisting of quarternery phosphonium salt and quarterneryammonium salt.

8. A process as claimed in claim 6, wherein quaternary salts are tetra butyl ammonium bromide and tetra butyl ammonium hydrogen sulphate.

9. A process as claimed in claim 1, wherein the ester is selected from a group consisting of ethyl acetate, butyl acetate, amyl acetate, and 2-ethyl hexyl acetate.

10. A process as claimed in claim 1, wherein the ester is ethyl acetate.

11. A process as claimed in claim 1, wherein quenching the reaction mass with urea.

12. A process as claimed in claim 1, wherein the pH is ranging between 3.2 to 4.3.

13. A process as claimed in claim 1, wherein maintaining the pH with acetic acid.

14. A process as claimed in claim 1, wherein filtering the solutions with filter paper.

15. A process as claimed in claim 1, wherein the oleoresin is marigold oleoresin.

16. A process as claimed in claim 1, wherein the triturating alcohol is ethyl alcohol.

17. A process as claimed in claim 1, wherein the stable lutein is of about 35% assay.

18. A process as claimed in claim 1, wherein the stabilizing material is non water-soluble fractions of reaction mixture of hydrolysis obtained after distillation of the alcohol.

19. A process as claimed in claim 1, wherein the Lutein fraction obtained from step (g) is blended with non-water-soluble fractions of reaction mixture of hydrolysis to obtain a stable Lutein paste.

20. A process as claimed in claim 1, wherein the stabilized Lutein stays at ambient conditions for a period of at least 6 months without any degradation.

21. A process as claimed in claim 1, wherein the lutein of step (i) stays at ambient conditions.

* * * * *